United States Patent
Schütz et al.

(10) Patent No.: US 12,127,915 B2
(45) Date of Patent: Oct. 29, 2024

(54) WOUND DRESSING

(71) Applicant: Essity Hygiene and Health Aktiebolag, Gothenburg (SE)

(72) Inventors: Patrick Schütz, Hamburg (DE); Christian Schulze, Hamburg (DE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 18/254,982

(22) PCT Filed: Dec. 17, 2020

(86) PCT No.: PCT/EP2020/086899
§ 371 (c)(1),
(2) Date: May 30, 2023

(87) PCT Pub. No.: WO2022/128115
PCT Pub. Date: Jun. 23, 2022

(65) Prior Publication Data
US 2023/0338197 A1      Oct. 26, 2023

(51) Int. Cl.
*A61F 13/02* (2024.01)
*A61F 13/0206* (2024.01)
*A61F 13/0246* (2024.01)

(52) U.S. Cl.
CPC ...... *A61F 13/0289* (2013.01); *A61F 13/0206* (2013.01); *A61F 13/0253* (2013.01)

(58) Field of Classification Search
CPC .............. A61F 13/0289; A61F 13/0206; A61F 13/0253
See application file for complete search history.

(56) References Cited

U.S. PATENT DOCUMENTS

| | | |
|---|---|---|
| 11,007,082 B2 | 5/2021 | Tumey |
| 2004/0126413 A1 | 7/2004 | Sigurjonsson et al. |
| | (Continued) | |

FOREIGN PATENT DOCUMENTS

| | | |
|---|---|---|
| CN | 102112078 A | 6/2011 |
| CN | 102985134 A | 3/2013 |
| | (Continued) | |

OTHER PUBLICATIONS

International Search Report & Written Opinion for International Application No. PCT/EP2020/086899; International Filing Date: Dec. 17, 2020; Date of Mailing: Sep. 17, 2021; 11 pages.
(Continued)

*Primary Examiner* — Jessica Arble
(74) *Attorney, Agent, or Firm* — CANTOR COLBURN LLP

(57) ABSTRACT

The present invention relates to a wound dressing comprising or consisting of (a) a covering layer; (b) a sheath on the wound facing side of the covering layer, (c) an absorbent core within the sheath, and (d) an adherent layer on the wound facing side of the sheath; wherein the sheath comprises (b1) an adhesive sheath layer, (b2) a proximal sheath layer on the proximal sides of the absorbent core and the adhesive sheath layer and (b3) a distal sheath layer on the distal sides of the absorbent core and the adhesive sheath layer; wherein the adherent layer comprises an opening, and wherein the adherent layer has (i) a wound facing proximal side adapted to adhere to a body part, and (ii) a distal side adhering to an outer rim of the covering layer.

26 Claims, 2 Drawing Sheets

(56) References Cited

U.S. PATENT DOCUMENTS

| | | | |
|---|---|---|---|
| 2013/0018341 A1* | 1/2013 | Carlucci | A61F 13/533 604/365 |
| 2014/0058309 A1 | 2/2014 | Addison et al. | |
| 2014/0309574 A1 | 10/2014 | Cotton | |
| 2015/0320605 A1 | 11/2015 | Pigg et al. | |
| 2016/0067107 A1* | 3/2016 | Cotton | A61L 15/26 602/44 |
| 2016/0199528 A1* | 7/2016 | Tönnessen | A61L 15/24 604/372 |
| 2017/0079846 A1 | 3/2017 | Locke et al. | |
| 2017/0312406 A1 | 11/2017 | Svensby | |
| 2019/0344549 A1* | 11/2019 | Casu | B32B 5/08 |
| 2021/0196525 A1* | 7/2021 | Bishop | A61F 13/0213 |
| 2022/0062059 A1* | 3/2022 | Merckel | A61F 13/0209 |

FOREIGN PATENT DOCUMENTS

| | | |
|---|---|---|
| CN | 105492032 A | 4/2016 |
| CO | 2017001409 A2 | 7/2017 |
| EP | 1985270 A2 | 10/2008 |
| EP | 2851044 A1 | 3/2015 |
| EP | 3669838 A1 | 6/2020 |
| EP | 3669843 A1 | 6/2020 |
| GB | 201306317 | 5/2013 |
| GB | 2512841 A | 10/2014 |
| GB | 2537840 A | 11/2016 |
| WO | 2020126903 A1 | 6/2020 |

OTHER PUBLICATIONS

International Preliminary Report on Patentability for International Application No. PCT/EP2020/086899; International Filing Date: Dec. 17, 2020; Date of Mailing: Nov. 14, 2022; 9 pages.
Notice of Allowance issued in MX/a/2023/007172 dated Sep. 21, 2023, 6 pages.
Chinese Application No. 202080108001.1; Office Action with English translation dated Feb. 2, 2024; 17 pages.
Notice of Allowance issued in Colombia Application No. NC2023/0007899 dated May 17, 2024.

* cited by examiner

WOUND DRESSING

CROSS REFERENCE TO RELATED APPLICATIONS

This application is a National Stage application of PCT/EP2020/086899, filed Dec. 17, 2020, which is incorporated by reference in its entirety herein.

TECHNICAL FIELD

The present disclosure relates to an absorbent dressing for attachment to a body part and use in the treatment of skin wounds, in particular wounds showing strong exudation.

BACKGROUND

When skin or other tissue is wounded, the wound usually starts emitting exudate. The exudate comprises liquid leaking out of blood or lymph vessels and may contain serum, fibrin and leukocytes. Wounds which comprise areas of strong infection or inflammation can exude high fluid volumes. To manage these volumes, the wounds are often covered with wound dressings which comprise an absorbent core that can take up substantial amounts of fluid. Thereby, the fluid can be removed from the wound while the wound is kept moist, thus, promoting wound healing.

These absorbent cores can comprise, for example, super-absorbent particles as described e.g. in EP 1 985 270 A2. Some superabsorbers can bind up to a factor 1000 of their own weight in fluids. Superabsorbent-containing wound dressings are, therefore, particularly effective. However, in taking up the liquid, the superabsorbent particles and, hence, the absorbent cores increase considerably in volume. Specific attention, thus, needs to be paid to the design of the wound dressing, so that it can contain the absorbent core despite its increasing volume.

It has been suggested in the past to use an elastic covering layer to contain the increased volume while keeping the wound dressing attached to the wound. When the volume of the absorbent core increases, the covering layer is stretched and expands together with the absorbent core. Alternatively or additionally, the absorbent core in the dressing can be exchangeable. Some dressings provide additional space for the absorbent core to expand into by encasing the core in a larger sheath.

Notwithstanding these improvements, the structural integrity of dressings for highly exudating wounds can suffer from the extreme increase in volume leading to delamination of individual dressing layers. Moreover, the stretching of the covering layer during expansion can lead to diminished adherence strength.

There is, thus, a need in the art for improved absorbent wound dressings which can take up large volumes of exudate and at the same time adhere to the area around the wound site.

SUMMARY

This problem is solved by an absorbent dressing as described in the appended claims. The dressing is sealed in a particularly secure manner and provides enough space within the dressing for the expansion of the absorbent core when taking up fluids. Drawbacks of the dressings known in the art are thereby overcome.

In a first aspect, the invention relates to a wound dressing comprising or consisting of (a) a covering layer; (b) a sheath on the wound facing side of the covering layer, (c) an absorbent core within the sheath, and (d) an adherent layer on the wound facing side of the sheath; wherein the sheath comprises (b1) an adhesive sheath layer, (b2) a proximal sheath layer on the proximal sides of the absorbent core and the adhesive sheath layer and (b3) a distal sheath layer on the distal sides of the absorbent core and the adhesive sheath layer; wherein the adherent layer comprises an opening, and wherein the adherent layer has (i) a wound facing proximal side adapted to adhere to a body part, and (ii) a distal side adhering to an outer rim of the covering layer.

The wound dressing is a medical dressing able to absorb fluids, such as wound fluids. It is, thus, an absorbent dressing. The wound dressing can be adapted to be used on skin, e.g. human skin, and will, consequently adhere to the skin of the wearer, e.g. to the skin of a patient.

In an exemplary embodiment, the wound dressing is a unitary dressing, rendering it unnecessary for the medical personnel applying the dressing to assemble the dressing from several components before its application. Instead, all components of the wound dressing described herein form a unit that holds together without the use of further components or supporting tools.

The wound dressing comprises (b) a sheath on the wound facing side of the covering layer, i.e. the proximal side of the covering layer. The words "proximal" and "distal" are used herein to refer to the position of the respective surface in relation to the wearer when the wound dressing is worn. In line with the standard meaning of the terms in the art, "distal" refers to the surface which is farther away from the wearer and "proximal" refers to the surface which is closer to the wearer, i.e. closer to the wound, skin and/or other body surface.

The sheath is a closed body enveloping an inner sheath space. Within that inner sheath space, the absorbent core is arranged. The inner sheath space is surrounded completely by the proximal and distal sheath layers. As described herein below, the sheath may be closed by sealing the outer edges of at least the proximal and distal layers of the sheath. In an exemplary embodiment, this may be achieved by sealing the outer edges of the proximal and distal sheath layers and of the adhesive sheath layer. In an exemplary embodiment, the outer edges of the proximal and distal sheath layers are sealed together with the adhesive sheath layer arranged between them.

The sheath, hence, comprises (b1) an adhesive sheath layer, (b2) a proximal sheath layer on the proximal sides of the absorbent core and the adhesive sheath layer and (b3) a distal sheath layer on the distal sides of the absorbent core and the adhesive sheath layer. The sheath may consist of the aforementioned layers, i.e. of the adhesive sheath layer, and the proximal and distal sheath layers. It is, nevertheless, also possible to add further layers to the sheath, for example to increase the absorptive capacity and/or the structural integrity of the sheath.

The adhesive sheath layer comprised in the sheath is adapted to connect the proximal and distal sheath layers with each other, in particular the outer edges of the proximal and distal sheath layers. For this purpose, at least parts of the adhesive sheath layer can be arranged in between the outer edges of the proximal and distal sheath layers. The outer edges (outer rims) of the three layers may be sealed to each other around the entire circumference of the sheath. That way, it is ensured that the absorbent core is securely held within the closed sheath. Accordingly, in an exemplary embodiment, the outer edges of the adhesive sheath layer, the proximal sheath layer and the distal sheath layer are connected by sealing, such as heat-sealing, to form the sheath. The "circumference" is in a plane that is substantially parallel to the adherent layer, e.g. the middle plane of the sheath.

The adhesive sheath layer can essentially be of the same shape and size as the proximal and/or distal sheath layers. For example, all three layers may have a rectangular shape with rounded corners. Alternatively, all three layers may have a circular, ellipsoid or the same irregular shape. The adhesive sheath layer having this shape and size can have— but does not have to have—an opening in its middle. The opening in the adhesive sheath layer and the absorbent core may have essentially the same shape, e.g. both a rectangular, circle, oval or the same irregular shape. exemplary shapes include a rectangular shape with rounded edges. The opening in the adhesive sheath layer can help in modulating the flow of wound fluids from the sheath layers, in particular the proximal sheath layer, to the absorbent core.

In some exemplary embodiments, the adhesive sheath layer does not have an opening in its middle. Depending on the material of the adhesive sheath layer, the presence of a central region of the adhesive sheath layer between the proximal sheath layer and the absorbent core can enhance the flow of wound fluids to the absorbent core or slow the uptake of wound fluids down. An adhesive sheath layer that has essentially the same shape and size as the proximal and/or distal sheath layers, i.e. no opening in its middle, can also simplify the manufacturing process of the dressing. Moreover, such an adhesive sheath layer that is continuous between the absorbent core and the proximal sheath layer can reduce the pressure that the expanding absorbent core exerts onto the wound.

It will be understood that, in an exemplary embodiment, the adhesive sheath layer is liquid-permeable, in particular in embodiments in which it is located between the absorbent core and the proximal sheath layer. Since the adhesive sheath layer is liquid permeable, the wound exudate can pass through said layer and reach more distally located layers such as the absorbent core. Permeability to liquids, in particular wound exudate, can be achieved by different strategies. For example, the adhesive sheath layer can have pores, perforations or incisions. The pores, perforations or incisions enable the passage of liquid through the layer. Alternatively, the adhesive sheath layer can be a fibrous web or non-woven fabric. The open structure of the fibrous web and/or non-woven fabric enables the passage of fluids through the layer. In one embodiment, the adhesive sheath layer is a fibrous web, i.e. a layer having the structure of a fibrous web. The term "fibrous web" used herein refers to a web or net consisting of or comprising fibers. The fibers can be short fibers, such as fibers having an average length of 10 mm or less, 5 mm or less, 3 mm or less or 1 mm or less.

The adhesive sheath layer may be between the proximal sheath layer and the absorbent core or between the distal sheath layer and the absorbent core, wherein the former alternative may be desirable. Presence of the adhesive sheath layer between the proximal sheath layer and the absorbent core can increase the mechanical resistance on the proximal side of the absorbent core. It was found that the absorbent core, thus, extends away from the wound site to a greater extend. The pressure exerted by the expanding absorbent core is, thus, reduced.

The adhesive sheath layer comprises or consists of an adhesive that is adapted to connect the sheath layers which are arranged on opposite sides of the adhesive sheath layer. This means that the adhesive sheath layer either comprises adhesive layers on its proximal as well as its distal side or that it is an adhesive layer in its entirety (e.g. soaked through with an adhesive or consisting of an adhesive). The adhesive sheath layer can also be named 'fusible layer'. As indicated above, in an exemplary embodiment the adhesive sheath layer consists of an adhesive. It can, for example, be an adhesive web. The adhesive sheath layer can, for example, consist of or comprise co-polyamide or co-polyester, wherein co-polyamide may be desirable.

The adhesive sheath layer may comprise or consist of an adhesive that is solid at room temperature, but tacky when molten (hotmelt adhesive), e.g. a co-polyamide or co-polyester adhesive. These adhesives are usually solid at room temperature to body temperature, i.e. in at least a range of 20° C. to 40° C. At higher temperatures, usually temperatures above 100° C., the adhesive melts. It hardens upon cooling. The hotmelt adhesive used in the adhesive sheath layer of the invention may have a melting temperature of 100° C. or more, such as 120° C. or more. In an exemplary embodiment, however, the melting temperature of the hotmelt adhesive may be lower than 200° C. in order to avoid damaging of other dressing components. Accordingly, the hotmelt adhesive may desirably has a melting temperature of 200° C. or less, 180° C. or less, or 160° C. or less. In other words, the hotmelt adhesive may have a melting temperature of from 100° to 200° C., 100° to 160° C., 110° C. to 150° C., such as about 130° C. Suitable hotmelt adhesives are known in the art. The adhesive sheath layer can, e.g., be a fibrous web consisting of or comprising a co-polyamide or co-polyester hotmelt adhesive having a melting temperature of from 100° C. to 160° C.

The adhesive sheath layer may be relatively lightweight. For example, the adhesive sheath layer may have a weight of from 4 to 20 g/m$^3$, or more specifically from 6 to 15 g/m$^3$, such as from 8 to 12 g/m$^3$.

In a second, related aspect, the invention, accordingly, relates to a method for producing a wound dressing according to any of the preceding claims, comprising steps of heat-sealing the sheath through the covering layer. The method advantageously allows the wound dressing to be manufactured in a short time and facilitates straightforward and economic manufacture. All layers of the wound dressing can be stacked on top of each other and the sheath can subsequently be sealed through the covering layer, i.e. heat can be applied to all layers including the covering layer and the adherent layer.

The sealing between the adhesive sheath layer, the proximal sheath layer and the distal sheath layer in the wound dressing according to the invention forms a sealed edge in the sheath. The sealed edge may run around the entire circumference of the sheath in a plane that is substantially parallel to the adherent layer. The sealed edge can have a width of from 0.5 cm to 3 cm, from 0.8 cm to 2.5 cm, or from 1 cm to 1.8 cm. In other words, the sealed edge can have a width of 0.5 cm or more, 0.75 cm or more, 1 cm or more. The width of the sealed edge can be the same around the entire circumference of the sheath.

The sheath layers and the adhesive sheath layer may have a length and width of e.g. from 2 cm to 40 cm, from 3 cm to 30 cm, from 4 to 25 cm, or from 6 cm to 10 cm. For example, the sheath layers and the adhesive sheath layer can have a substantially square shape with a width and length of about 9 to 11 cm.

Proximally or distally of the adhesive sheath layer (c) an absorbent core is arranged within the sheath. The absorbent core has distal and proximal surfaces. The distal surface of the absorbent core is adjacent to the distal sheath layer or to the adhesive sheath layer. The proximal surface of the absorbent core is adjacent to the proximal sheath layer or to the adhesive sheath layer. Usually, the absorbent core will not be attached to the sheath layers or to the adhesive sheath layer so that it is relatively free to move inside the sheath and not restricted in its expansion during the uptake of wound fluids.

The absorbent core comprises or consists of one or more absorbent materials. Accordingly, the core is able to take up and retain fluids, such as wound fluids (exudate).

The term "wound fluids" or "exudate" refers to fluids which have escaped from a wound, in particular because of inflammatory processes of the blood plasma. The wound fluids or exudates serve to supply the wound bed and the healing processes which are taking place there with a wide array of components, including nutrients for fibroblasts and epithelial cells, growth factors and cytokines. The wound fluids also assist in the cleaning of the wound and the degradation of damaged tissue.

The absorbent core is a flat layer that usually comprises a woven or non-woven fabric to stabilise the absorbent materials structurally and/or functionally support the absorbent materials comprised in the core. Non-woven materials are fabric-like materials made from short and/or long fibres bonded together by chemical, mechanical, heat or solvent treatment. The non-woven can e.g. be manufactured by milling the fibres. Exemplary non-woven fabrics include airlaid fabrics, which is a non-woven material made of cellulose and polyolefin fibers.

The absorbent material(s) may be embedded in the flat layer, e.g. in the woven or non-woven material. The absorbent materials may e.g. be superabsorbent materials, such as one or more superabsorbent materials selected from the group consisting of superabsorbent fibers and superabsorbent particles. In one embodiment, the absorbent core is an airlaid mat containing a cellulose nonwoven with embedded superabsorbent particles.

Due to the improved structural integrity and reduced risk of a delamination, the absorbent core can be relatively thick. The core can, e.g. have a thickness of 1 mm or more, or 2 mm or more, when it is dry. In other words, the thickness of the absorbent core can be from 1 mm to 10 mm, such as from 2 mm to 5 mm. The thickness of the absorbent core can increase considerably during fluid uptake, e.g. up to 5 cm or more. In other words, the thickness of the absorbent core can increase 10-fold or more during fluid uptake.

The absorbent core can have a rectangular (such as square) shape, e.g. a rectangular shape with rounded edges; an oval shape; a round shape or an irregular shape. The term "shape" as mentioned herein, refers to the shape that can be seen when looking at the absorbent core or other part of the wound dressing described herein from proximal or distal direction, i.e. the shape in an XY-plane, wherein the XY-plane is substantially parallel to the skin or surface of the body part on which the wound dressing can be worn, i.e. substantially parallel to the adhesive layer.

Usually, the shape of the absorbent core will be substantially identical to that of the sheath and the wound dressing. For example, a rectangular wound dressing can comprise a rectangular sheath and a rectangular absorbent core; an oval wound dressing can comprise an oval sheath and an oval absorbent core. It will be understood that the core will be smaller than the sheath in XY-plane, i.e. smaller than the sheath layers and the adhesive sheath layer.

The absorbent core may have a length and width of e.g. from 1 cm to 35 cm, from 2 cm to 30 cm, or from 3 to 20 cm. For example, an absorbent core can have a square shape with a width and length of from 3 to 5 cm, such as 4 cm. In particular embodiments, the absorbent core can have a square shape with a width and length of from 2 to 6 cm, the sheath layers and the adhesive sheath layer can have a square shape with a width and length of from 6 to 10 cm.

As indicated above, the sheath comprises in addition to the adhesive sheath layer also (b2) a proximal sheath layer on the proximal sides of the absorbent core and the adhesive sheath layer and (b3) a distal sheath layer on the distal sides of the absorbent core and the adhesive sheath layer.

The sheath layers, in particular the proximal sheath layer are liquid permeable layers. The material of the sheath layers will support the fluid uptake by the absorbent core, e.g. by slowing the uptake of fluid, increasing the speed of uptake or even adding further absorptive capacity. In an exemplary embodiment, the sheath layers increase the speed of fluid uptake from the wound to the absorbent core, e.g. by making use of capillary forces in the sheath layers or the like.

Due to the opening in the underlying adhesive layer, at least a part of the proximal sheath layer may be in direct contact with the wound and/or skin of the wearer. This means that at least a middle area of the proximal sheath layer may be adapted to be in direct contact with the body part on which the wound dressing is worn. The proximal and, optionally, also the distal sheath layer will therefore have a good biocompatibility and will be a material that can easily be removed from wet wound tissue.

Certain absorbent materials are known to develop adherence to the wound bed. This adherence is considered detrimental, since it usually leads to pain and damage of the newly formed wound tissue during dressing removal, thereby delaying healing. The material of the proximal and, optionally, also the distal sheath layer may therefore be a low-adherent material, such as may be selected from the group of low-adherent materials consisting of polymer films or fabrics (woven or non-woven), which may be treated in a way to render them less adherent to the wound. Commercial products comprising non-adherent or low-adherent layers are e.g. Profore™ WCL (sold by Smith&Nephew), Mepitel® (sold by Mölnlycke Health Care). The term "low-adherent" material is herein used to describe materials which have a lower adherence to a wound bed than the absorbent core.

The proximal sheath layer and/or the distal sheath layer may, e.g., comprise or consist of a woven or non-woven material, wherein the latter may be desirable. The non-woven can e.g. consist of or comprise of a material selected from the group consisting of polypropylene, polyester, co-polyester and combinations thereof. The non-woven material can be spun-bound. The material can have a filament-laid structure.

In order to allow the absorbent core to expand within the sheath, the outer dimensions of the unwetted absorbent core are smaller than the inner dimensions of the sheath.

The sheath encloses an inner sheath space that has an inner sheath area extending parallel to the adherent layer within the flat-lying and unwetted absorbent dressing. The inner sheath space is the volume of the room inside the sheath when no absorbent core and adhesive sheath layer would be present within the space and the layers of the wound dressing are not elastically or plastically deformed. The inner sheath space is, thus, limited on the proximal side by the proximal sheath layer, on the distal side by the distal sheath layer and laterally by the sealed outer edge.

The inner sheath area is one cross-section of the inner sheath space at its maximal expansion. Usually, the inner sheath area is substantially identical to the area of the part of the sheath layers which is not partaking in the sealed outer edge. The inner sheath area can have a size of from 2 cm² to 1500 cm², from 4 cm² to 840 cm², from 9 cm² to 570 cm², or from 15 cm² to 80 cm², such as e.g. 25 cm².

The absorbent core has an outer area extending parallel to the adherent layer within the flat-lying and unwetted absorbent dressing. The outer area is the surface area of maximal expansion of the absorbent core in a plane that is substantially parallel to the absorbent layer. This outer area of the absorbent core can have a size of from 1 cm² to 1225 cm², from 4 cm² to 900 cm², ore from 9 cm² to 36 cm², such as 16 cm². In exemplary embodiments, the outer area of the absorbent core may, thus, be from 1 cm² to 1225 cm² and the inner sheath area from 2 cm² to 1500 cm².

It can be seen that the size of the outer area of the absorbent core is smaller than the size of the inner sheath area. The outer area of the absorbent core can e.g. be from 40% to 90% of the size of the inner sheath area (wherein the size of the inner sheath area is 100%), 45% to 85%, 50% to 80%, 55% to 75%, 60% to 70%, such as about 65%. In other words, the size of the outer area of the absorbent core is 90% or less of the size of the inner sheath area, 85% or less, 80% or less, 75% or less, 70% or less, 65% or less, wherein 75% or less may be desirable. All of the values mentioned herein refer to the wound dressing in an unwetted state if not specifically indicated otherwise.

The wound dressing according to the invention further comprises (a) a covering layer. The covering layer is located on the distal side of the sheath and, thus, farthest away from the wound and skin surface when the wound dressing is worn. As will be explained in more detail below, the covering layer in some embodiments has no direct contact to the surface of the skin of the wearer, because the adherent layer has essentially the same size and shape as the covering layer and is located between the covering layer and the surface of the skin or other body part to be treated over the entire area of the covering layer. There is, thus, no need to coat the covering layer with an adhesive to stick to the skin or other body part to be treated. The covering layer can be entirely free of adhesives. The cohesion between the covering layer and the other layers of the dressing is ensured by the adhesive comprised in the adherent layer (further described elsewhere herein).

The covering layer can be highly flexible to allow for an increase in volume of the absorbent core and, consequently, the sheath. The covering layer can be stretched and, for this purpose, comprises a stretchable material. The material can be elastically and/or plastically stretchable. The covering layer may have a tensile strength of from 15 to 30 N/25 mm. It can have an elongation of from 400% or more, or 500% or more.

The covering layer can be liquid-impermeable, specifically water-impermeable. At the same time, it can be vapor permeable. This ensures that no wound fluid leaks to the outside of the dressing, but that the dressing has a good breathability.

Suitable materials which have the aforementioned properties are known in the art. The covering layer may, for example, consist of or comprise a material selected from the group consisting of polyurethane and co-polyester, wherein a polyurethane is desirable. The polyurethane may be a thermoplastic polyurethane or a non-thermoplastic polyurethane.

The thickness of the covering layer ensures the desired flexibility as well as the desired stability of the covering layer. The layer can have a weight of from 15 to 35 g/m², or 20 to 30 g/m².

The wound dressing according to the invention further comprises (d) an adherent layer on the wound facing side of the sheath. While the wound dressing may comprise further layers than those described above (covering layer; absorbent core; sheath consisting of distal sheath layer, adhesive sheath layer, and proximal sheath layer; and adherent layer), in particular embodiments, the dressing consists of these layers.

The wound dressing's adherent layer comprises an opening, through which fluid can pass from the wound into the absorbent core. Usually, the opening will be substantially in the centre of the adherent layer resulting in a frame shape or frame-like shape of the adherent layer. The adherent layer may be liquid impermeable.

The opening and the absorbent core may have essentially the same shape, e.g. both a rectangular, circle, oval or the same irregular shape. Desirable shapes include a rectangular shape with rounded edges. Within the wound dressing, the absorbent core is aligned with the opening. The term "aligned" in this context means that the absorbent core is arranged distally from the opening and that an axis which is orthogonal to the absorbent core as well as the adherent layer is a shared middle axis of opening and absorbent core. A "middle axis" is an axis crossing the respective entity in its middle.

The area of the opening, i.e. its size, can be 50% or more of the area of the absorbent core, such as 60% or more, 70% or more, 80% or more, 90% or more, 100% or more, 110% or more. In other words, the area of the opening can be from 50% to 150%, from 60% to 140%, from 70% to 130%, or from 80% to 120% of the area of the absorbent core. The size of the opening and the size of the absorbent core in a plane parallel to the adherent layer can, thus, be substantially identical.

Importantly, the size of the opening in the adherent layer will usually be smaller than the size of the sheath in a plane parallel to the adherent layer. In other words, the size of the opening in the adherent layer will be smaller than the size of the proximal sheath layer. Thereby, it is ensured that the sheath is safely held within the wound dressing.

Within the wound dressing, the sheath is aligned with the opening. The term "aligned" in this context means that the sheath is arranged distally from the opening and that an axis which is orthogonal to the sheath, specifically the absorbent core within the sheath, as well as to the adherent layer is a shared middle axis of opening and the sheath.

An outer edge of the sheath—which may be an outer edge that is broader, identical or narrower than the outer edge of the sheath which is sealed as described above—may be covered by the adherent layer, desirably around the entirety of the opening in the adherent layer.

The adherent layer has (i) a wound facing proximal side adapted to adhere to a body part, and (ii) a distal side adhering to an outer rim of the covering layer.

The adherent layer can comprise a first adhesive on its proximal side. The first adhesive is adapted to adhere to the surface of a body part, such as the skin, of a wearer. It furthermore ensures that the dressing can be removed from the skin substantially without harming the surface of the body part. It has been discovered that a particularly suitable first adhesive is an adhesive which comprises a silicone.

To ensure a firm attachment of the dressing to the skin of the wearer—also during expansion of the absorbent core—the first adhesive has a high adhesion to steel value, such as from 0.5 N/cm to 0.8 N/cm, or from 0.6 to 0.7 N/cm.

The adherent layer may comprise a second adhesive on its distal side. The second adhesive is suitable to adhere to the covering layer in an outer rim region of the covering layer. The second adhesive e.g. an acrylic adhesive. Alternative adhesives are known in the art.

To be able to adhere to the adherent layer, the covering layer is larger than the sheath and protrudes over the sheath on all sides. The outer rim may be shaped like a frame with the sheath in its middle. The outer rim of the covering layer may have a width of from e.g. 0.5 cm to 4 cm, 0.75 cm to 3 cm, 0.9 cm to 2 cm. In other words, the outer rim can be 0.5 cm or more, 0.75 cm or more, or 1 cm or more.

BRIEF DESCRIPTION OF FIGURES

Exemplary embodiments of the invention are shown schematically in the drawings.

These and other aspects of the invention will be apparent from and elucidated with reference to the embodiments described hereinafter.

DESCRIPTION OF EMBODIMENTS

Additional advantages, characteristics, and features of the present invention will become clear from the following detailed description of exemplary embodiments with reference to the attached drawings. However, the invention is not restricted to these exemplary embodiments.

Figure 1:
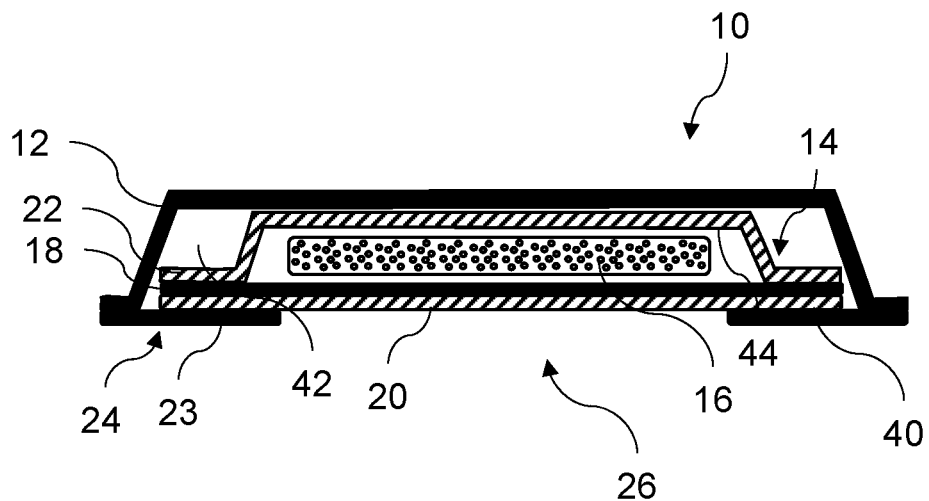
FIG. 1 schematically shows a wound dressing according to the present invention, in which the adhesive sheath layer is on the proximal side of the absorbent core.
Figure 2:
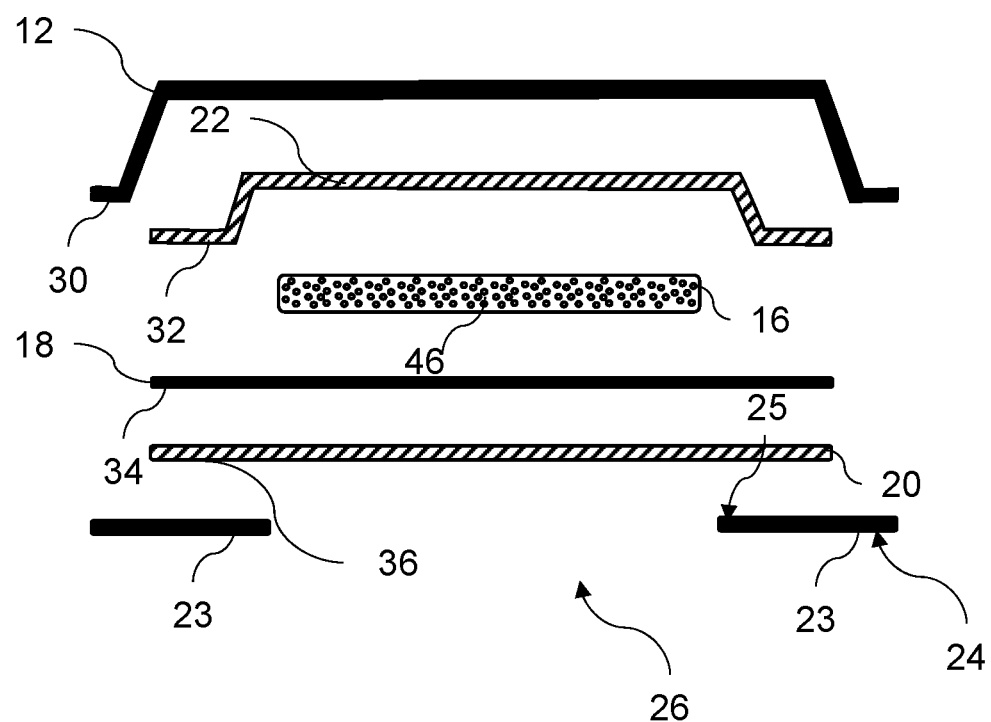
FIG. 2 shows an exploded view of the wound dressing of FIG. 1.

FIGS. 1 and 2 schematically show a side view and an exploded side view of a wound dressing 10 according to the present invention, in which the adhesive sheath layer 18 is on the proximal side of the absorbent core 16. The wound dressing 10 comprises a flexible, elastic PU covering layer 12, a sheath 14 and an adherent layer 23.

The sheath 14 consists—from proximal to distal direction—of a proximal sheath layer 20, adhesive sheath layer 18, absorbent core 16 and distal sheath layer 22. The proximal sheath layer 20 and the distal sheath layer 22 consist of a spunbound non-woven polypropylene. The adhesive sheath layer 18 consists of fibrous web formed by co-polyamide. The absorbent core 16 is an airlaid with superabsorbent particles and cellulose fibers having a thickness of about 1.25 mm.

The proximal sheath layer 20, adhesive sheath layer 18, absorbent core 16 and distal sheath layer 22 are aligned with each other, i.e. they share a common middle axis. The proximal sheath layer 20, adhesive sheath layer 18 and distal sheath layer 22 are substantially identical in size. The outer area 46 of the absorbent core 16 is about 64% of the size of the inner sheath area 44. The sheath 14 provides an inner sheath space 42 that has a larger volume than the unwetted absorbent core 16.

The proximal sheath layer 20, distal sheath layer 22 and adhesive sheath layer have been fused together along their outer edges 32, 34, 36 (see FIG. 2). For this purpose, the adhesive sheath layer 18 comprises a hotmelt adhesive. For fusing the layers, all layers (covering layer 12, distal sheath layer 22, absorbent core 16, adhesive sheath layer 18, proximal sheath layer 24 and adherent layer 23 have been placed on top of each other in the correct order. Subsequently, heat in the range of from 120° C. to 160° C. was applied to the outer edges 32, 34, 36 through the covering layer 12 generating a sealed edge 40.

The sheath 14 is enclosed by second sheath that is established by the covering layer 12 and the adherent layer 23 which are attached to each other. The adherent layer 23 comprises an opening 26 in its middle that is aligned with the absorbent core 16. The opening 26 is slightly larger than the absorbent core 16 in its maximal extension in a plane that is parallel to the adherent layer 23. The sheath 14 is slightly larger than the opening 26 ensuring that the absorbent core 16 is securely held inside the wound dressing 10.

The frame-shaped adherent layer 23 has an acrylic adhesive on its distal side 25 so that it adheres to an outer area of the proximal sheath layer 20 and an outer rim 30 of the covering layer. Further, the adherent layer 23 has a silicone adhesive on its proximal side 24 so that it is adapted to adhere to a body part (not shown).

Figure 3:
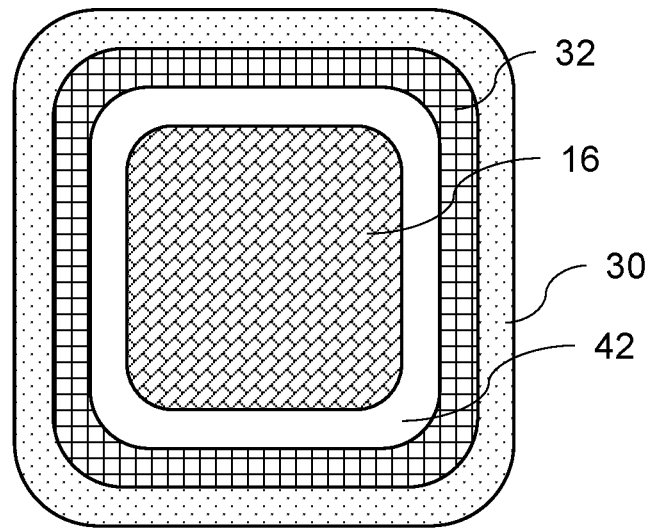
FIG. 3 schematically shows a top view of the wound dressing of FIG. 1.

FIG. 3 schematically shows a top view of the wound dressing of FIG. 1 which shows covering layer 12 in a top view. Since the covering layer 12 is transparent, the layers underneath it can also be seen. The outer rim 30 of the covering layer 12 runs around the entire circumference of the covering layer 12. Next to it, the sealed outer edge 32 of the sheath 14 can be seen. Next to this heat-sealed part of the sheath 14 and between the absorbent core 16 and the sealed outer edge 32, the free inner sheath space 42 can be seen.

Figure 4:
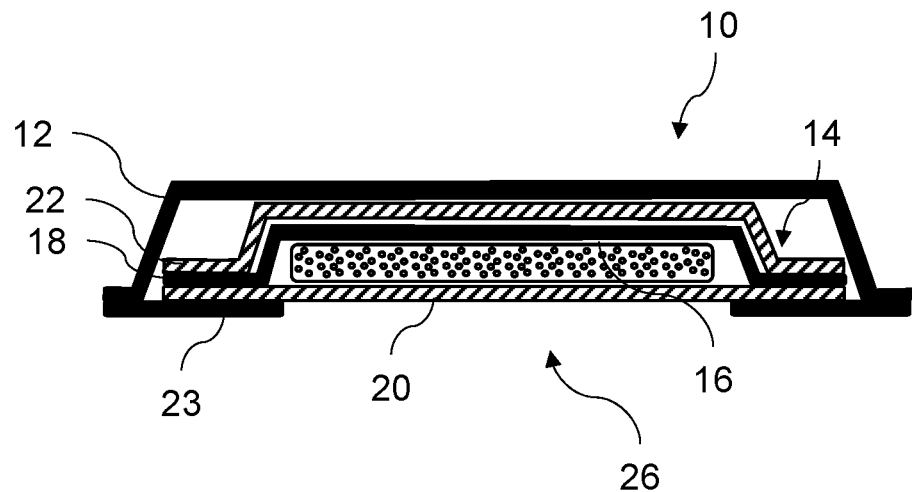
FIG. 4 schematically shows an alternative wound dressing according to the present invention, in which the adhesive sheath layer is on the distal side of the absorbent core.

FIG. 4 schematically shows an alternative wound dressing 10 according to the present invention, in which the adhesive sheath layer 18 is on the distal side of the absorbent core 16. Apart from this difference, the wound dressing 10 is essentially the same as shown in FIGS. 1 to 3.

Figure 5:
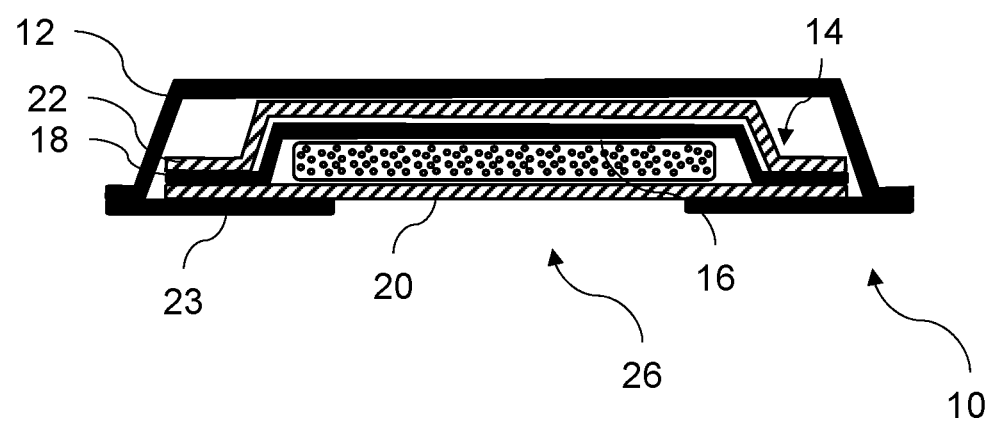
FIG. 5 schematically shows a further alternative wound dressing according to the present invention, in which the size of the opening in the adherent layer is smaller than the size of the absorbent core.

FIG. 5 schematically shows a further alternative wound dressing 10 according to the present invention, in which the size of the opening 26 in the adherent layer is smaller than the size of the absorbent core 16. Apart from this difference, the wound dressing 10 is essentially the same as shown in FIG. 4.

The invention claimed is:

1. A wound dressing comprising:
 (a) a covering layer;
 (b) a sheath on the wound facing side of the covering layer,
 (c) an absorbent core within the sheath, and
 (d) an adherent layer on the wound facing side of the sheath;
 wherein the sheath comprises:
  (b1) an adhesive sheath layer,
  (b2) a proximal sheath layer on the proximal sides of the absorbent core and the adhesive sheath layer and
  (b3) a distal sheath layer on the distal sides of the absorbent core and the adhesive sheath layer;
 wherein an opening is defined in the adherent layer such that an entirety of the absorbent core overlaps the opening and the absorbent core does not overlap the adherent layer,
 wherein the adherent layer has
  (i) a wound facing proximal side adapted to adhere to a body part, and
  (ii) a distal side adhering to an outer rim of the covering layer, and wherein the adhesive sheath layer is positioned at least partially within the covering layer and between the absorbent core and the proximal sheath layer as a flat sheet.

2. The wound dressing according to claim 1, wherein the adhesive sheath layer comprises a hotmelt adhesive.

3. The wound dressing according to claim 1, wherein the adhesive sheath layer is a fibrous web layer.

4. The wound dressing according to claim 1, wherein outer edges of the adhesive sheath layer, the proximal sheath layer, and the distal sheath layer are connected by sealing to form the sheath.

5. The wound dressing according to claim 4, wherein the sealing forms a sealed edge having a width of from 0.5 cm to 3 cm.

6. The wound dressing according to claim 1, wherein the adherent layer comprises a first adhesive on its proximal side.

7. The wound dressing according to claim 1, wherein the adherent layer comprises a second adhesive on its distal side.

8. The wound dressing according to claim 1, wherein the absorbent core is aligned with the opening.

9. The wound dressing according to claim 1, wherein the area of the opening is from 100% to 120% of the area of the absorbent core.

10. The wound dressing according to claim 1, wherein the proximal sheath layer and/or the distal sheath layer comprise a non-woven material.

11. The wound dressing according to claim 1, wherein the sheath encloses an inner sheath space that has an inner sheath area extending parallel to the adherent layer within the flat-lying and unwetted absorbent dressing; the absorbent core has an outer area extending parallel to the adherent layer within the flat-lying and unwetted absorbent dressing; and the size of the outer area of the absorbent core is from 40% to 90% of the size of the inner sheath area.

12. The wound dressing according to claim 11, wherein the outer area of the absorbent core is from 50% to 80% of the size of the inner sheath area.

13. The wound dressing according to claim 11, wherein the outer area of the absorbent core is from 1 500 mm2 to 60 000 mm2 and the inner sheath area is from 2 400 mm2 to 70 000 mm2.

14. The wound dressing according to claim 1, wherein the covering layer comprises a material selected from the group consisting of polyurethane and co-polyester.

15. The wound dressing according to claim 1, wherein the covering layer is liquid-impermeable.

16. The wound dressing according to claim 1, wherein the covering layer has a weight of from 15 to 35 g/m2.

17. The wound dressing according to claim 1, wherein the covering layer has a tensile strength of from 15 to 30 N/25 mm.

18. The wound dressing according to claim 1, wherein the covering layer has an elongation of from 400% or more.

19. A method for producing a wound dressing according to claim 1, comprising steps of heat-sealing the sheath through the covering layer.

20. The wound dressing according to claim 2, wherein the hotmelt adhesive has a melting temperature of from 100° to 160° C.

21. The wound dressing according to claim 1, wherein outer edges of the adhesive sheath layer, the proximal sheath layer, and the distal sheath layer are connected by heat-sealing to form the sheath.

22. The wound dressing according to claim 4, wherein the sealing forms a sealed edge having a width of from 1 cm to 1.8 cm.

23. The wound dressing according to claim 1, wherein the adherent layer comprises a first adhesive comprising a silicone on its proximal side.

24. The wound dressing according to claim 1, wherein the adherent layer comprises a second adhesive that is an acrylic adhesive on its distal side.

25. The wound dressing according to claim 1, wherein the covering layer has a weight of from 20 to 30 g/m2.

26. The wound dressing according to claim 1, wherein the covering layer has an elongation of from 500% or more.

* * * * *